(12) United States Patent
Allen et al.

(10) Patent No.: US 6,204,039 B1
(45) Date of Patent: Mar. 20, 2001

(54) PLANT ISOCITRATE DEHYDROGENASE HOMOLOGS

(75) Inventors: Stephen M. Allen, West Chester, PA (US); Saverio Carl Falco, Arden, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/196,520

(22) Filed: Nov. 19, 1998

Related U.S. Application Data

(60) Provisional application No. 60/067,388, filed on Dec. 2, 1997.

(51) Int. Cl.[7] ..................................................... C12N 9/04
(52) U.S. Cl. ........................... 435/190; 435/6; 435/69.1; 435/410; 435/325; 435/252.3; 435/91.2; 435/320.1; 435/25; 530/23.2
(58) Field of Search ................... 435/69.1, 190, 435/325, 6, 410, 252.3, 91.2, 320.1, 25; 530/23.2, 25.4

(56) References Cited

U.S. PATENT DOCUMENTS 5,482,845   1/1996   Soares et al. .................... 435/91.1

OTHER PUBLICATIONS

Hodges M., Submitted EMBL/Genbank/DDBJ database, Acession #X96727, Apr. 2, 1998.
Jackson et al., Mol. Gen. Genet. 236: 309–314 Accession #P29696, Dec. 1992.
Branch, TIBS, 23:45–50, Feb. 1998.
Cupp et al., (1991), J. Biol. Chem., 266:22199–22205.
Behal, et al, NAD + dependent isocitrate dehydrogenase from *Arabidopsis thaliana*. Characterization of two closely related subunits, *Plant Molecular Biology*, 36, 691–698, 1998.
Jackson, et al, Cloning and expression analysis of β–isopropylmalate dehydrogenase from potato, *Molecular General Genetics*, 236, 309–314, 1993.
EMBL Databank, Accession No. AB005240, XP–002101722, Jul. 18, 1997.
EMBL Databank, Accession No. C19133, XP002101723, Oct. 25, 1996.
C. A. McIntosh, Partial purification and characteristics of membrane–associated NAD+ dependent isocitrate dehydrogenase activity from etiolated pea mitochindria, *Plant Science*, 129, 9–20, 1997.
Keys et al., (1990), Bacteriol., 172:4280–4287.
Nichols et al., (1995), Biochem J., 310:917–922.
Alvarez–Villafane et al., (1996), Biochemistry, 35:4741–4752.
Galvez et al., (1995), Plant Sci., 105:1–14.
Chen et al., (1990), Plant Physiol. Biochem., 28:141–145.
Genbank Accession No. X67310.
NCBI Accession No. gi 3021506.
Plant Journal, 16(3), pp. 325–333, (1998).
Cupp et al., (1991), J. Biol. Chem., 266:22199–22205.*
Martinez–Rivai et al., (1998), Plant Physiol., 118:249–255.*

* cited by examiner

*Primary Examiner*—Rebecca E. Prouty
*Assistant Examiner*—Richard Hutson

(57) ABSTRACT

This invention relates to an isolated nucleic acid fragment encoding an isocitrate dehydrogenase. The invention also relates to the construction of a chimeric gene encoding all or a portion of the isocitrate dehydrogenase, in sense or antisense orientation, wherein expression of the chimeric gene results in production of altered levels of the isocitrate dehydrogenase in a transformed host cell.

19 Claims, 1 Drawing Sheet

Fig. 1

```
                   1                                                          60
Potato IPMDH      MALQIAKRLLRCRADSVASSVRFF...DRTFT.SESNSNLIRATLFPGDGIGPEIAESVR
Tobacco IDH       MAFQIARRLLRSRA...SSSIRYL...DRSFS.SESNSNLIRATLFPGDGIGPEIADSVR
Wheat contig      MAL...RRLLQGIV...LPRTTGR...HVGASFSTEAGETIRATLFPGDGIGPEIAESVK
crln.pk0061.f9    MAL...RRLLQGSV...LPRIIGRDLAPAVAPFSTESGETIRATLFPGDGIGPEIAESVK
rls6.pk0004.b3    MAL...RRLLQGSV...LPRMAGR...AAAAPFSTASGETVRATLFPGDGIGPEIAESVK
ssm.pk0072.e6Z    MA....SQLLRRTF...GCRILAN...PRAFSFSSAASTPIRATLFPGDGIGPEIAESVK 61                                                         120
Potato IPMDH      QIFKVAEVPIEWEEHYVGTEVDPRTNSFLTWESLESVRRNKVGLKGPMATPIGKGHRSLN
Tobacco IDH       QIFKTAEVPIEWEEHYVGKEIDPRTNSFLTWESLESVRRNKVGLKGPMATPIGKGHRSLN
Wheat contig      QVFNVAGVPIEWEEHYVGTEVDPRTESFLTWESLESVRRNKVGLKGPMATPIGKGHRSLN
crln.pk0061.f9    QVFNVAGVPIEWEEHYVGTEVDPRTESFLTWESLESVRRNKVGLKGPMATPIGKGHRSLN
rls6.pk0004.b3    QVFNVAXVPIEWEEHYVGTEVDPRTESFLTWESLESVRRNKVGLKGPMATPIGKGHRSLN
ssm.pk0072.e6Z    QIFQAADVPIEWEEHYVXTEIDPRTQSFLTWESLESVRQNGVGLKGPMATPIGKGHRSLN 121                                                        180
Potato IPMDH      LTLRKELNLYANVRPCYSLPGYKTRYDDVNLITIRENTEGEYSGLEHQVVRGVVESLKII
Tobacco IDH       LTLRKELNLYANVRPCYSLPGYKTRYDDVNLITIRENTEGEYSGVEHQVVRGVVESLKII
Wheat contig      LTLRKELGLYANVRPCNSLPGYKTRYDDVNLVTIRENTEGEYSGLEHQVVRGVVESLKII
crln.pk0061.f9    LTLRKELGLYANVRPCNSLPGYKTRYDDVNLVTIRENTEGEYSGLEHQVVRGVVESLKII
rls6.pk0004.b3    LTLRKELGLYANVRPCNSLPGYKTRYDDVNLVTIRENTEGEYSGLEHQVVRGVVESLKII
ssm.pk0072.e6Z    LTLRKELNLYANVRPCYSLPGYKTRYDNVNLITIRENTEGEYSGLEHQVVRGVVESLKII 181                                                        240
Potato IPMDH      TRQASLRVAEYAFHYAKTHGRERVSAIHKANIMQKTDGLFLKCCREVAEKYPEIKYEEVV
Tobacco IDH       TRQASLRVAEYAFHYAKAHGRERVSAIHKANIMQKTDGLFLKCCREVAEKYPEIKYEEVV
Wheat contig      TRQASLRVAEYAFHYAKANGRERVSAIHKANIMRKTDGLFLKCCREVAEKYPEITYEEVI
crln.pk0061.f9    TRQASLRVAEYAFHYAKANGRERVSAIHKANIMRKTDGLFLKCCREVSEKYPEIQYEEVI
rls6.pk0004.b3    TRQASLRVAEYAFHYAKTNGRERVSAIHKANIMRKTDGLFLKCCREVAEKYPEIVYEEVI
ssm.pk0072.e6Z    TRQASLRVAEYAFHYAKAHGRERVSAIHKANIMQKTDGLFLKCCREVAEKYPEITYEEVV 241                                                        300
Potato IPMDH      IDNCCMMLVKNPALFDVLVMPNLYGDIISDLCAGLIGGLGLTPSCNIGEGGIALAEAVHG
Tobacco IDH       IDNCCMMLVKNPALFDILVMPNLYGDIISDLCAGVIGGLGLTPSCNIGEGGIALAEAVHG
Wheat contig      IDNCCMTLVKNPGTFDVLVMPNLYGDIISDLCAGLIGGLGLTPSCNIGEGGICLAEAVHG
crln.pk0061.f9    IDNCCMTLVKNPALFDVLVMPNLYGDIISDLCAGLIGGLGLTPSCNIGEGGICLAEAVHG
rls6.pk0004.b3    IDNCCMTLVKNPGLFDVLVMPNLYGDIISDLCAGLIGGLGLTPSCNIGEGGICLAEAVHG
ssm.pk0072.e6Z    IDNCCMMLVKNPALFDVLVMPNLYGDIISDLCAGLVGGLGLTPSCNIGEGGIALAEAVHG 301                                                        360
Potato IPMDH      SAPDIAGKNLANPTALLLSSVSMLRHLELHDKADRIQDAILKTIAGGK...........V
Tobacco IDH       SAPDIAGKNLANPTALLLSAVTMLRHLELHDKADRIQGAVLNTIAEGKYRTGDLGGTSST
Wheat contig      SAPDISGKNLANPTALMLSAVTMLRHLQFNDKQADRIHNAILQTIAEGKYRTADLGGKSST
crln.pk0061.f9    SAPDIAGKNLANPTALMLSAVMLLRHMQFNDKADRIHNAILQTIAEGKYRTADLGGKAST
rls6.pk0004.b3    SAPDIAGKNLANPTALMLSAVMMLRHLQFNNQADRIHNAILQTISEGKFRTADLGGKAST
ssm.pk0072.e6Z    SAPDIAGKNLANPTALLLSGVTMLRHLNLHDKAEQIQKAILNTIAEGKYRTADLGGSSKT 361         378
Potato IPMDH      PNWRPWRHCYNN......
Tobacco IDH       TD.......FTNAICDHL
Wheat contig      SD.......YTKAVCDHI
crln.pk0061.f9    SE.......FTNAVCDHI
rls6.pk0004.b3    SD.......FTKAVCDHI
ssm.pk0072.e6Z    TE.......FTKAIIDHL
```

PLANT ISOCITRATE DEHYDROGENASE HOMOLOGS

This application claims priority benefit of U.S. Provisional Application No. 60/067,388 filed Dec. 2, 1997, now pending.

FIELD OF THE INVENTION

This invention is in the field of plant molecular biology. More specifically, this invention pertains to nucleic acid fragments encoding AND+ isocitrate dehydrogenase in plants and seeds.

BACKGROUND OF THE INVENTION

AND+ isocitrate dyhdrogenase (AND+ IDH; EC 1.1.1.41) is a key step in the citric acid cycle and catalyzes the oxidative decarboxylation of isocitrate to form α-ketoglutarate, $CO_2$, and NADH. Its key regulatory role in the TCA cycle is well documented. Traditionally the enzyme was also considered to be responsible for the production of 2-oxoglutarate which is a precursor in ammonia assimilation and amino acid biosynthesis (Bray (1983) Nitrogen Metabolism in Plants. Longman, London); however, NADP+ IDH (EC 1.1.1.42) has recently been regarded as an alternative pathway when large quantities of 2-oxoglutarate are required (Chen et al. (1990a) *Plant Physiol Biochem* 28:141–145; Gàlvez et al. (1995) *Plant Sci* 105:1–14).

AND+ IDH is localized exclusively in the mitochondria in association with the TCA cycle. This enzyme has been purified from several nonphotosynthetic eukaryotes such as fungi (Keys et al. (1990) *Bacteriol* 172:4280–4287; Alvarez-Villafañe et al. (1996) *Biochemistry* 35:4741–4752) and animals (Giorgio et al. (1970) *J. Biol Chem* 245:5469–5477), in which it appears to be a 300-kD octamer. AND-IDH cDNAs have been cloned from yeast (Cupp et al. (1991) *J. Biol Chem* 266: 22199–22205) and animals (Nichols et al. (1995) *Biochem J* 310:917–922). In these organisms, the enzyme is composed of two (yeast) or more (animals) different subunits encoded by different genes.

Accordingly, the availability of nucleic acid sequences encoding all or a portion of an isocitrate dehydrogenase would facilitate studies to better understand carbon and nitrogen metabolic pathways in plant cells and provide genetic tools to enhance or otherwise alter these pathways which in turn could provide mechanisms to modulate the citric acid cycle and possibly ammonia assemilation in plant cells. Additionally, the instant isocitrate dehydrogenase proteins can be used as a targets to facilitate design and/or identification of inhibitors of those enzymes that may be useful as herbicides.

SUMMARY OF THE INVENTION

The instant invention relates to isolated nucleic acid fragments encoding an enzyme of the citric acid cycle. Specifically, this invention concerns an isolated nucleic acid fragment encoding an isocitrate dehydrogenase. In addition, this invention relates to a nucleic acid fragment that is complementary to the nucleic acid fragment encoding an isocitrate dehydrogenase.

An additional embodiment of the instant invention pertains to a polypeptide encoding all or a substantial portion of an isocitrate dehydrogenase. In another embodiment, the instant invention relates to a chimeric gene encoding an isocitrate dehydrogenase, or to a chimeric gene that comprises a nucleic acid fragment that is complementary to a nucleic acid fragment encoding an isocitrate dehydrogenase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an isocitrate dehydrogenase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an isocitrate dehydrogenase in a transformed host cell comprising: a) transforming a host cell with a chimeric gene comprising a nucleic acid fragment encoding an isocitrate dehydrogenase; and b) growing the transformed host cell under conditions that are suitable for expression of the chimeric gene wherein expression of the chimeric gene results in production of altered levels of isocitrate dehydrogenase in the transformed host cell.

An addition embodiment of the instant invention concerns a method for obtaining a nucleic acid fragment encoding all or a substantial portion of an amino acid sequence encoding an isocitrate dehydrogenase.

A further embodiment of the instant invention is a method for evaluating at least one compound for its ability to inhibit the activity of an isocitrate dehydrogenase, the method comprising the steps of: (a) transforming a host cell with a chimeric gene comprising a nucleic acid fragment encoding an isocitrate dehydrogenase, operably linked to suitable regulatory sequences; (b) growing the transformed host cell under conditions that are suitable for expression of the chimeric gene wherein expression of the chimeric gene results in production of isocitrate dehydrogenase in the transformed host cell; (c) optionally purifying the isocitrate dehydrogenase expressed by the transformed host cell; (d) treating the isocitrate dehydrogenase with a compound to be tested; and (e) comparing the activity of the isocitrate dehydrogenase that has been treated with a test compound to the activity of an untreated isocitrate dehydrogenase, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 shows a comparison of the amino acid sequences of potato isopropylmalate dehydrogenase (IPMDH), tabacco isocitrate dehydrogenase (IDH), cr1n.pk0061.f9, rls6.pk0004.b3, ssm.pk0072.e6 and the wheat contig composed of cDNA clones wle1n.pk0059.36 and wl1.pk0012.c2.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the entire cDNA insert in clone cr1n.pk0061.f9 encoding an entire corn isocitrate dehydrogenase.

SEQ ID NO:2 is the deduced amino acid sequence of an isocitrate dehydrogenase derived from the nucleotide sequence of SEQ ID NO:1.

SEQ ID NO:3 is the nucleotide sequence comprising the entire cDNA insert in clone rls6.pk0004.b3 encoding an entire rice isocitrate dehydrogenase.

SEQ ID NO:4 is the deduced amino acid sequence of an isocitrate dehydrogenase derived from the nucleotide sequence of SEQ ID NO:3.

SEQ ID NO:5 is the nucleotide sequence comprising the entire cDNA insert in clone ssm.pk0072.e6 encoding an entire soybean isocitrate dehydrogenase.

SEQ ID NO:6 is the deduced amino acid sequence of an isocitrate dehydrogenase derived from the nucleotide sequence of SEQ ID NO:5.

SEQ ID NO:7 is the nucleotide sequence of a contig assembled form the entire cDNA insert in clone encoding an entire soybean isocitrate dehydrogenase.

SEQ ID NO:8 is the deduced amino acid sequence of an isocitrate dehydrogenase derived from the nucleotide sequence of SEQ ID NO:7.

SEQ ID NO:9 is the amino acid sequence of a *Nicotiana tabacum* isocitrate dehydrogenase.

SEQ ID NO:10 is the amino acid sequence of a *Solanum tuberosum* isocitrate dehydrogenase misidentified as isopropylmalate dehydrogenase.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence. As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar nucleic acid sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences encode proteins that are 90% identical to the amino acid sequences reported herein. Most preferred are nucleic acid fragments that are 95% identical to the coding sequence of the nucleic acid fragments reported herein. Sequence percent identity calculations were performed by the Jotun Hein method (Hein. J. J. (1990) *Meth. Enz.* 183:626–645) using the Megalign program of the LASARGENE bioinformatics computing suite (DNASTAR Inc., Madison, Wis.). Default parameters for the Jotun Hein method for multiple alignments are: GAP PENALTY=11, GAP LENGTH PENALTY=3; for pairwise alignments KTUPLE 2.

A "substantial portion" of an amino acid comprises enough of the amino acid sequence to code for a functional polypeptide and afford putative identification of that polypeptide either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). A "substantial portion" of a nucleotide sequence comprises enough of the nucleotide sequence to encode a functional polypeptide and afford putative identification of that polypeptide either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/).

In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the isocitrate dehydrogenase proteins as set forth in SEQ ID NOs: 2, 4, 6 and 8. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Maniatis").

Nucleic acid fragments encoding at least a portion of several isocitrate dehydrogenase proteins have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Isocitrate Dehydrogenase Proteins

| Enzyme | Clone | Plant |
| --- | --- | --- |
| Isocitrate dehydrogenase | cr1n.pk0061.f9 | Corn |
| | r1s6.0004.b3 | Rice |
| | ssm.pk0072.e6 | Soybean |
| | w1e1n.pk0059.e6 | Wheat |
| | w11n.pk0012.c2 | |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other isocitrate dehydrogenase proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed isocitrate dehydrogenase proteins are present at higher or lower levels than normal or in cell types or developmental stages in which they are not normally found. This would have the effect of altering the level of activity of the citric acid cycle in those cells.

Overexpression of the isocitrate dehydrogenase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provide. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant isocitrate dehydrogenase to different cellular compartments, or to facilitate its secretion from the cell. It is thus envisioned that the chimeric gene described above may be further supplemented by altering the coding sequence to encode isocitrate dehydrogenase with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding isocitrate dehydrogenase in plants for some applications. In order to accomplish this, a chimeric gene designed for co-suppression of the instant isocitrate dehydrogenase proteins can be constructed by linking a gene or gene fragment encoding an isocitrate dehydrogenase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant isocitrate dehydrogenase proteins (or portions thereof) may be produced in heterologous host cells, particularly in the cells of microbial hosts, and can be used to prepare antibodies to the these proteins by methods well known to those skilled in the art. The antibodies are useful for detecting isocitrate dehydrogenase in situ in cells or in vitro in cell extracts. Preferred heterologous host cells for production of the instant isocitrate dehydrogenase are microbial hosts. Microbial expression systems and expression vectors containing regulatory sequences that direct high level expression of foreign proteins are well known to those skilled in the art. Any of these could be used to construct a chimeric gene for production of the instant isocitrate dehydrogenase proteins. This chimeric gene could then be introduced into appropriate microorganisms via transformation to provide high level expression of the encoded isocitrate dehydrogenase. An example of a vector for high level expression of the instant isocitrate dehydrogenase proteins in a bacterial host is provided (Example 6).

Additionally, the instant isocitrate dehydrogenase proteins can be used as a targets to facilitate design and/or identification of inhibitors of those enzymes that may be useful as herbicides. This is desirable because the isocitrate dehydrogenase proteins described herein catalyze the conversion of isocitrate and AND to α-ketoglutarate and NADH and $CO_2$ in the citric acid acid cycle a key pathway of aerobic metabolism. Accordingly, inhibition of the activity of one or more of the enzymes described herein could lead to inhibition plant growth. Thus, the instant isocitrate dehydrogenase proteins could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1): 37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the isocitrate dehydrogenase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding an isocitrate dehydrogenase can be identified and obtained. This mutant plant can then be used to determine or confirm the natural function of the isocitrate dehydrogenase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
| --- | --- | --- |
| cr1n | Corn root from 7 day old seedlings* | cr1n.pk0061.f9 |
| r1s6 | Rice leaf 15 days after germination, 6 hours after infection of strain *Magaporthe grisea* 4360-R-67 (AVR2-YAMO); Susceptible | r1s6.0004.b3 |
| ssm | Soybean shoot meristem | ssm.pk0072.e6 |
| w1e1n | Wheat leaf from 7 day old etiolated seedling* | w1e1n.pk0059.e6 |
| w1l n | Wheat leaf from 7 day old seedling* | w1l n.pk0012.c2 |

*These libraries were normalized essentially as described in U.S. Pat. No. 5,482,845, incorporated herein by reference cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding isocitrate dehydrogenase proteins were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272 and Altschul, Stephen F., et al. (1997) *Nucleic Acids Res.* 25:3389–3402) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Corn, Rice, Soybean and Wheat Isocitrate Dehydroyenase The BLASTX search using the nucleotide sequences from clones cr1n.pk0061.f9, rls6.pk0004.b3, ssm.pk0072.e6 and wl1.pk0012.c2 revealed similarity of the peptides encoded by the cDNAs to the potato 3-isopropylmalate dehydrogenase (GenBank Accession No. X67310). However, more detailed sequence analysis indicates that the potato 3-isopropylmalate dehydrogenase (GenBank accession No. X67310) was misidentified and is actually isocitrate dehydrogenase because of its strong sequence homology (92% similarity at the amino acid level) to a *Nicotiana tabacum* (NCBI Identifier No. gi3021506) isocitrate dehydrogenase sequence (FIG. 1). The potato 3-isopropylmalate dehydrogenase (GenBank accession No. X67310) was not biochemically characterized. The initial BLAST results for each of these ESTs against the potato sequence are shown in Table 3:

TABLE 3

BLAST Results for Clones Encoding Polypeptides Homologous to Isopropylmalate Dehydrogenase

| Clone | BLAST pLog Score X67310 |
| --- | --- |
| cr1n.pk0061.f9 | 23.85 |
| rls6.pk0004.b3 | 26.48 |
| ssm.pk0072.e6 | 75.82 |
| wl1.pk0012.c2 | 111.37 |

The sequence of the entire cDNA insert in clone cr1n.pk0061.f9 was determined and is shown in SEQ ID NO:1; the deduced amino acid sequence of this cDNA is shown in SEQ ID NO:2. The amino acid sequence set forth in SEQ ID NO:2 was evaluated by BLASTP, yielding a pLog value of 175.00 versus the *Nicotiana tabacum* (NCBI Identifier No. gi3021506) isocitrate dehydrogenase sequence.

The sequence of the entire cDNA insert in clone rls6.pk0004.b3 was determined and is shown in SEQ ID NO:3; the deduced amino acid sequence of this cDNA is shown in SEQ ID NO:4. The amino acid sequence set forth in SEQ ID NO:4 was evaluated by BLASTP, yielding a pLog value of 173.00 versus the *Nicotiana tabacum* (NCBI Identifier No. gi3021506) isocitrate dehydrogenase sequence.

The sequence of the entire cDNA insert in clone ssm.pk0072.e6 was determined and is shown in SEQ ID NO:5; the deduced amino acid sequence of this cDNA is shown in SEQ ID NO:6. The amino acid sequence set forth in SEQ ID NO:6 was evaluated by BLASTP, yielding a pLog value of >220.00 versus the *Nicotiana tabacum* (NCBI Identifier No. gi3021506) isocitrate dehydrogenase sequence.

The sequence of the entire cDNA insert in clone wl1.pk0012.c2 was determined and subsequently found to have overlapping homology with the cDNA sequence of clone wle1n.pk0059.e6. Using this homology it was possible to align the sequences and assemble a contig (a contig is an assemblage of overlapping nucleic acid sequences to form one contiguous nucleotide sequence). The individual sequences were assembled into a contiguous nucleotide sequence encoding a wheat isocitrate dehydrogenase protein. The sequence of the assembled contig is shown in SEQ ID NO:7; the deduced amino acid sequence of this cDNA is shown in SEQ ID NO:8. The amino acid sequence set forth in SEQ ID NO:8 was evaluated by BLASTP, yielding a pLog value of >220.00 versus the *Nicotiana tabacum* (NCBI Identifier No. gi3021506) isocitrate dehydrogenase sequence.

FIG. 1 presents an alignment of the amino acid sequences set forth in SEQ ID NOs:2, 4, 6 and 8 and the *Nicotiana tabacum* (NCBI Identifier No. gi 3021506) isocitrate dehydrogenase sequence. Also included in FIG. 1 is the potato 3-isopropylmalate dehydrogenase (GenBank accession No. X67310) amino acid sequence to show the degree of similarity between the *Nicotiana tabacum* and potato sequences.

The data in Table 4 represents a calculation of the percent similarity of the amino acid sequences set forth in SEQ ID NOs:2, 4, 6 and 8 and the *Nicotiana tabacum* (NCBI Identifier No. gi 3021506) isocitrate dehydrogenase sequence.

TABLE 4

Percent Similarity of Amino Acid Sequences Deduced From the Nucleotide Sequences of cDNA Clones Encoding Polypeptides Homologous to Isocitrate Dehydrogenase

| Clone | SEQ ID NO. | Percent Similarity to *Nicotiana tabacum* isocitrate dehydrogenase |
| --- | --- | --- |
| cr1n.pk0061.f9 | 2 | 82.6% |
| rls6.pk0004.b3 | 4 | 81.5% |
| ssm.pk0072.e6 | 6 | 87.5% |
| Contig composed of: wle1n.pk0059.e6 wl1.pk0012.c2 | 8 | 82.6% |

Sequence alignments were performed by the Lipman-Pearson method of alignment (Lipman, D. J. and Pearson, W. R. (1985) *Science* 227:1435–1441), using the Megalign program of the LASARGENE bioinformatics computing suite (DNASTAR Inc., Madison, Wis.). Sequence percent similarity calculations were performed by the Jotun Hein method (Hein. J. J. (1990) *Meth. Enz.* 183:626–645) using the Megalign program of the LASARGENE bioinformatics computing suite (DNASTAR Inc., Madison, Wis.).

Sequence alignments and BLAST scores and probabilities indicate that the instant nucleic acid fragments encode entire or nearly entire isocitrate dehydrogenase proteins. These sequences represent the first corn, rice, soybean and wheat sequences encoding isocitrate dehydrogenase proteins.

Example 4

Expression of Chimeric Genes in Monocot Cells

A chimeric gene comprising a cDNA encoding an isocitrate dehydrogenase in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding an isocitrate dehydrogenase, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al., (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant isocitrate dehydrogenase proteins in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding an isocitrate dehydrogenase. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) Nature (London) 327:70, U.S. Pat. No. 4,945,050). A Du Pont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al.(1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the isocitrate dehydrogenase and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant isocitrate dehydrogenase proteins can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5' -CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as decribed above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the isocitrate dehydrogenase proteins are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Isocitrate Dehydrogenase The isocitrate dehydrogenase proteins described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant isocitrate dehydrogenase proteins may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant isocitrate dehydrogenase proteins, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the isocitrate dehydrogenase proteins are expressed as fusion proteins, the purification protocol may include the use of an affinity resin which is specific for the fusion protein tag attached to the expressed enzyme or an affinity resin containing ligands which are specific for the enzyme. For example, an isocitrate dehydrogenase protein may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activition of the isocitrate dehydrogenase disclosed herein. Assays may be conducted under well known experimental conditions which permit optimal enzymatic activity. For example, assays for isocitrate dehydrogenase activity are presented by Martinez-Rivai et al. (1998) *Plant Physiol* 118:249–255.

What is claimed is:

1. An isolated polynucleotide selected from the group consisting of:
   (a) SEQ ID NO:1, SEQ ID NO:3, SEQ ID NO:5 or SEQ ID NO:7;
   (b) a nucleic acid sequence encoding a polypeptide selected from the group consisting of SEQ ID NO:2, SEQ ID NO:4, SEQ ID NO:6, or SEQ ID NO:8; and
   (c) a nucleic acid sequence that is complementary to (a) or (b).

2. A chimeric nucleic acid sequence comprising the isolated polynucleotide of claim 1 operably linked to one or more suitable regulatory sequences.

3. A transformed host cell comprising the chimeric nucleic acid sequence of claim 2.

4. A method of altering the level of expression of an isocitrate dehydrogenase polypeptide in a host cell comprising:
   (a) transforming a host cell with the chimeric nucleic acid sequence of claim 2; and
   (b) growing the transformed host cell of step (a) under conditions that are suitable for expression of the chimeric nucleic acid sequence;
   wherein expression of the chimeric nucleic acid sequence results in production of altered levels of isocitrate dehydrogenase polypeptide in the transformed host call.

5. A method of obtaining an isolated polynucleotide encoding an isocitrate dehydrogenase polypeptide comprising:
   (a) probing a cDNA or genomic library with at least 30 contiguous nucleotides of the isolated polynucleotide of claim 1;
   (b) isolating the DNA clone or genomic DNA which hybridizes in step a; and
   (c) sequencing the cDNA or genomic DNA that comprises the clone isolated in step (b)
   wherein the sequenced cDNA or genomic DNA encodes an isocitrate dehydrogenase.

6. A method of obtaining an isolated polynucleotide encoding an isocitrate dehydrogenase polypeptide comprising:
   (a) synthesizing an oligonucleotide primer corresponding to at least 30 contiguous nucleotides of the isolated polynucleotide set forth in any of SEQ ID NOs:1, 3, 5, and 7; and
   (b) amplifying a cDNA insert present in a cloning vector using the oligonucleotide primer of step (a)
   wherein the amplified isolated polynucleotide encodes an isocitrate dehydrogenase polypeptide.

7. An expression cassette comprising an isolated polynucleotide of claim 1 operably linked to a promoter.

8. A method of positive selection of a transformed cell comprising:
(a) transforming a plant cell with the chimeric nucleic acid sequence of claim 2 or the expression cassette of claim 7; and
(b) growing the transformed plant under conditions allowing expression of the isolated polynucleotide in an amount sufficient to provide a positive selection means.

9. An isolated polynucleotide comprising a nucleic acid selected from the group consisting of:
(a) a polynucleotide that is at least 90% indentical by the Jotun Hein method of alignment to an isolated polynucleotide encoding the isocitrate dehydrogenase polypeptide set forth in a nucleic acid selected from the group consisting of SEQ ID NO: 2, SEQ ID NO: 6 and SEQ ID NO: 8, wherein the isolated polynucleotide encodes an isocitrate dehydrogenase polypeptide; and
(b) polynucleotide that is complementary to the polynucleotide of (a).

10. A chimeric nucleic acid sequence comprising the isolated polynucleotide of claim 9 operably linked to suitable regulatory sequences.

11. A transformed host cell comprising the chimeric nucleic acid sequence of claim 10.

12. A method of altering the level of expression of an isocitrate dehydrogenase polypeptide in a host cell comprising:
(a) transforming a host cell with the chimeric nucleic acid sequence of claim 10; and
(b) growing the transformed host cell of step (a) under conditions that are suitable for expression of the chimeric nucleic acid sequence wherein expression of the chimeric nucleic acid sequence results in production of altered levels of isocitrate dehydrogenase polypeptide in the transformed host cell.

13. A method of obtaining an isolated polynucleotide encoding an isocitrate dehydrogenase polypeptide comprising:
(a) probing a cDNA or genomic DNA library with at least 30 contiguous nucleotides of the isolated polynucleotide of claim 9;
(b) isolating the cDNA or genomic DNA identified in step (a); and
(c) sequencing the cDNA or genomic DNA;
wherein the isolated polynucleotide encodes an isocitrate dehydrogenase polypeptide.

14. A method of obtaining an isolated polynucleotide encoding an isocitrate dehydrogenase polypeptide comprising:
(a) synthesizing an oligonucleotide primer corresponding to at least 30 contiguous nucleotides of the isolated polynucleotide set forth in claim 9; and
(b) amplifying a cDNA insert present in a cloning vector using the oligonucleotide primer of step (a)
wherein the amplified DNA encodes an isocitrate dehydrogenase polypeptide.

15. An expression cassette comprising an isolated polynucleotide of claim 9 operably linked to a promoter.

16. A method of positive selection of a transformed cell comprising:
(a) transforming a plant cell with the chimeric nucleic acid sequence of claim 14 or the expression cassette of claim 15; and
(b) growing the transformed plant under conditions allowing expression of the isolated polynucleotide in an amount sufficient to provide positive selection means.

17. The method of claim 16 wherein the plant cell is a monocot.

18. The method of claim 16 wherein the plant cell is a dicot.

19. A method for evaluating at least one compound for its ability to inhibit the activity of an isocitrate dehydrogenase, the method comprising the steps of:
(a) transforming a host cell with a chimeric gene of claim 2 or 10;
(b) growing the transformed host cell under conditions that result in production of the isocitrate dehydrogenase;
(c) treating the isocitrate dehydrogenase either in vivo or in vitro with a compound to be tested; and
(d) comparing the activity of the isocitrate dehydrogenase that has been treated with a test compound to the activity of an untreated isocitrate dehydrogenase, thereby selecting compounds with potential for inhibitory activity.

* * * * *

SEQUENCE LISTING

<160> NUMBER OF SEQ ID NOS: 10

<210> SEQ ID NO 1
<211> LENGTH: 1501
<212> TYPE: DNA
<213> ORGANISM: Zea mays

<400> SEQUENCE: 1

```
ctcccccctc gtccgacctc ctcgccgccg cagacgaccg ccgccgccgc tgccgctgcc      60
gctgcgaacc ctttgtgaat cttcgttgtc cgggctgtgt ggggcaggca tggcgctccg     120
gaggctgctg caggggagcg tcctgccgcg gataatcggc agggatttgg caccggccgt     180
ggcgccgttt tcaacggagt ccggggagac cattcgtgcc acgctctttc ccggcgatgg     240
catcgggcca gagatcgctg agtctgtcaa gcaggtattc aatgttgcag gggtaccaat     300
tgaatgggaa gaacactatg tcggtacaga agttgatccc agaacagaga gtttttttgac     360 ttgggaaagc ctggagtcag tgcgtagaaa caaagttggc ttgaaaggac ctatggctac     420
```

```
acctattgga aagggccatc gatctttgaa tcttacatta aggaaagaac ttgggctcta    480
tgccaatgtc agaccttgca acagcctccc aggttacaag accagatacg atgatgttaa    540
ccttgtaaca attcgtgaaa atactgaagg agaatatagt ggtcttgagc atcaggttgt    600
gagaggtgtt gtggaaagtt tgaaaattat tacacgccaa gcaagtttga gagtggcaga    660
gtatgctttc cattatgcca aggccaatgg ccgggaaaga gtctctgcga tccacaaagc    720
caatattatg aggaagacag atggtctttt cctcaagtgt tgccgtgaag tgtctgaaaa    780
gtaccctgaa attcaatacg aggaggtcat cattgacaat tgctgtatga cgcttgtgaa    840
gaatcctggt cttttgacg tattagtgat gccaaatctc tatggtgaca ttattagtga    900
tctatgtgct ggtttgatcg ggggcttggg cctaacaccc agttgcaata ttggtgaagg    960
tggcatttgt ctggcagaag ctgttcatgg ttctgctcct gatattgctg caagaaacct   1020
cgcgaacccg actgctctta tgctgagtgc tgtcatgttg ttgcgccaca tgcaattcaa   1080
cgacaaagca gaccggatcc acaacgccat cctccagacc atcgccgagg ggaagtacag   1140
gactgctgat cttggtggaa aggcatcgac atcagagttt acaaacgcag tctgtgatca   1200
catctgagaa acggatgtga ttcttccttc tgattgtttt gtcatcctaa tatttttttg   1260
tcacatatga gaggagcttt agctttaaga ggttaactgg cagcacctcg aacttctttg   1320
gggtgtttaa cacggtttga gaccgtcaaa taattttgtc acatttcttg cggttcagaa   1380
attctttcaa cattggaatg gagccaagaa ttgtctgtaa taatcaacat cagcattata   1440
acagtatgta gggtttatct caaaaaaaaa aaaaaaaaaa aaaaaaaaaa aaaaaaaaaa   1500
a                                                                   1501
```

<210> SEQ ID NO 2
<211> LENGTH: 365
<212> TYPE: PRT
<213> ORGANISM: Zea mays

<400> SEQUENCE: 2

```
Met Ala Leu Arg Arg Leu Leu Gln Gly Ser Val Leu Pro Arg Ile Ile
  1               5                  10                  15

Gly Arg Asp Leu Ala Pro Ala Val Ala Pro Phe Ser Thr Glu Ser Gly
             20                  25                  30

Glu Thr Ile Arg Ala Thr Leu Phe Pro Gly Asp Gly Ile Gly Pro Glu
         35                  40                  45

Ile Ala Glu Ser Val Lys Gln Val Phe Asn Val Ala Gly Val Pro Ile
     50                  55                  60

Glu Trp Glu Glu His Tyr Val Gly Thr Glu Val Asp Pro Arg Thr Glu
 65                  70                  75                  80

Ser Phe Leu Thr Trp Glu Ser Leu Glu Ser Val Arg Arg Asn Lys Val
                 85                  90                  95

Gly Leu Lys Gly Pro Met Ala Thr Pro Ile Gly Lys Gly His Arg Ser
            100                 105                 110

Leu Asn Leu Thr Leu Arg Lys Glu Leu Gly Leu Tyr Ala Asn Val Arg
        115                 120                 125

Pro Cys Asn Ser Leu Pro Gly Tyr Lys Thr Arg Tyr Asp Asp Val Asn
    130                 135                 140

Leu Val Thr Ile Arg Glu Asn Thr Glu Gly Glu Tyr Ser Gly Leu Glu
145                 150                 155                 160

His Gln Val Val Arg Gly Val Val Glu Ser Leu Lys Ile Ile Thr Arg
                165                 170                 175
```

```
Gln Ala Ser Leu Arg Val Ala Glu Tyr Ala Phe His Tyr Ala Lys Ala
            180                 185                 190

Asn Gly Arg Glu Arg Val Ser Ala Ile His Lys Ala Asn Ile Met Arg
        195                 200                 205

Lys Thr Asp Gly Leu Phe Leu Lys Cys Cys Arg Glu Val Ser Glu Lys
    210                 215                 220

Tyr Pro Glu Ile Gln Tyr Glu Val Ile Ile Asp Asn Cys Cys Met
225                 230                 235                 240

Thr Leu Val Lys Asn Pro Gly Leu Phe Asp Val Leu Val Met Pro Asn
                245                 250                 255

Leu Tyr Gly Asp Ile Ile Ser Asp Leu Cys Ala Gly Leu Ile Gly Gly
            260                 265                 270

Leu Gly Leu Thr Pro Ser Cys Asn Ile Gly Glu Gly Ile Cys Leu
        275                 280                 285

Ala Glu Ala Val His Gly Ser Ala Pro Asp Ile Ala Gly Lys Asn Leu
    290                 295                 300

Ala Asn Pro Thr Ala Leu Met Leu Ser Ala Val Met Leu Leu Arg His
305                 310                 315                 320

Met Gln Phe Asn Asp Lys Ala Asp Arg Ile His Asn Ala Ile Leu Gln
                325                 330                 335

Thr Ile Ala Glu Gly Lys Tyr Arg Thr Ala Asp Leu Gly Gly Lys Ala
            340                 345                 350

Ser Thr Ser Glu Phe Thr Asn Ala Val Cys Asp His Ile
        355                 360                 365

<210> SEQ ID NO 3
<211> LENGTH: 1551
<212> TYPE: DNA
<213> ORGANISM: Oryza sativa

<400> SEQUENCE: 3
gttctaacac catcctctcc tcctcctccc ctttcccatc catctctctc tctctcctcc      60
tcctcgccgc cgaccgccgc cgccgccgcg agtcgccttc gccgtccggg tagcagcagg     120
aagagggagg aagggggggc atggcgctac ggaggctgct ccaggggagc gtcctgccgc     180
ggatggcggg cagagccgcc gcggcgccgt tctcgacggc gtccggggag accgtccgcg     240
ccacgctctt cccaggcgac ggcatcgggc ggagatcgc cgagtcggtc aagcaggtat     300
tcaatgttgc aggggtacca atagaatggg aagaacacta tgttggtaca gaagttgatc     360
ccagaacaga gagttttctg acttgggaaa gcttggagtc ggtgcggaga acaaagttg     420
gcttgaaagg tcctatggct acgcctattg aaaaggcca ccgttcattg aatcttacac      480
taaggaaaga gcttggtctt tatgcaaatg ttagaccttg caacagcctc ccaggataca     540
agactcgata tgatgatgtg aaccttgtga ctattcgtga aaataccgag ggagaatata     600
gtggccttga gcatcaggtt gtgagggtg ttgtggaaag cttaaaaatt atcactcgcc      660
aagcaagttt aagagtggca gagtatgctt ccactatgc caagaccaat ggccgggaga     720
gggtctctgc gatacacaag gccaatatca tgaggaagac cgatggtctt ttcctcaagt     780
gctgtcgtga agtggctgag aagtaccctg aaattgtata cgaggaggtc atcattgaca     840
attgttgtat gacgcttgtg aagaatcctg gtctttttga tgtactggtg atgccaaatc     900
tttatggtga tattattagt gatctttgt ctggtctgat tggaggcttg gcttgacac       960
ccagctgcaa cattggtgaa ggtggcattt gtctggcaga agctgttcac ggttctgctc    1020
ctgatattgc tggcaagaac cttgcaaacc cgaccgctct tatgctgagt gctgttatga    1080
```

-continued

```
tgttgcgcca cttgcaattc aataaccaag cagaccggat ccacaacgcc atcctccaga    1140
ccatctccga ggggaaattc aggactgctg atctcggcgg aaaggcgtcg acttcagact    1200
tcacgaaggc agtctgtgat catatctgat cgtccgatgt gattccgtcc tcttgattgt    1260
tttccttccc cctaattttt gttgcatacg cggagagaag ctttagcttt aagaggttaa    1320
ctggcggcac tcaatttct ttgggcttca gcatgggtta agaccaccta ataatcctgt     1380
cgcattcttg ctcttggaaa gtttcttcc aacattgcag tccagtcaga gaatggcctg     1440
taataattag tgacaaaatt atagcagtag atagaatctg ttcattcaag ttcttcaaat    1500
tactgggcca agcttcaatg tcattttttg cttaaaaaaa aaaaaaaaa a              1551
```

<210> SEQ ID NO 4
<211> LENGTH: 362
<212> TYPE: PRT
<213> ORGANISM: Oryza sativa
<220> FEATURE:
<221> NAME/KEY: UNSURE
<222> LOCATION: (58)

<400> SEQUENCE: 4

```
Met Ala Leu Arg Arg Leu Leu Gln Gly Ser Val Leu Pro Arg Met Ala
 1               5                  10                  15

Gly Arg Ala Ala Ala Pro Phe Ser Thr Ala Ser Gly Glu Thr Val
            20                  25                  30

Arg Ala Thr Leu Phe Pro Gly Asp Gly Ile Gly Pro Glu Ile Ala Glu
         35                  40                  45

Ser Val Lys Gln Val Phe Asn Val Ala Xaa Val Pro Ile Glu Trp Glu
     50                  55                  60

Glu His Tyr Val Gly Thr Glu Val Asp Pro Arg Thr Glu Ser Phe Leu
 65                  70                  75                  80

Thr Trp Glu Ser Leu Glu Ser Val Arg Arg Asn Lys Val Gly Leu Lys
                 85                  90                  95

Gly Pro Met Ala Thr Pro Ile Gly Lys Gly His Arg Ser Leu Asn Leu
            100                 105                 110

Thr Leu Arg Lys Glu Leu Gly Leu Tyr Ala Asn Val Arg Pro Cys Asn
        115                 120                 125

Ser Leu Pro Gly Tyr Lys Thr Arg Tyr Asp Asp Val Asn Leu Val Thr
    130                 135                 140

Ile Arg Glu Asn Thr Glu Gly Glu Tyr Ser Gly Leu Glu His Gln Val
145                 150                 155                 160

Val Arg Gly Val Val Glu Ser Leu Lys Ile Ile Thr Arg Gln Ala Ser
                165                 170                 175

Leu Arg Val Ala Glu Tyr Ala Phe His Tyr Ala Lys Thr Asn Gly Arg
            180                 185                 190

Glu Arg Val Ser Ala Ile His Lys Ala Asn Ile Met Arg Lys Thr Asp
        195                 200                 205

Gly Leu Phe Leu Lys Cys Cys Arg Glu Val Ala Glu Lys Tyr Pro Glu
    210                 215                 220

Ile Val Tyr Glu Glu Val Ile Ile Asp Asn Cys Cys Met Thr Leu Val
225                 230                 235                 240

Lys Asn Pro Gly Leu Phe Asp Val Leu Val Met Pro Asn Leu Tyr Gly
                245                 250                 255

Asp Ile Ile Ser Asp Leu Cys Ala Gly Leu Ile Gly Gly Leu Gly Leu
            260                 265                 270
```

```
Thr Pro Ser Cys Asn Ile Gly Glu Gly Ile Cys Leu Ala Glu Ala
            275                 280                 285

Val His Gly Ser Ala Pro Asp Ile Ala Gly Lys Asn Leu Ala Asn Pro
        290                 295                 300

Thr Ala Leu Met Leu Ser Ala Val Met Met Leu Arg His Leu Gln Phe
305                 310                 315                 320

Asn Asn Gln Ala Asp Arg Ile His Asn Ala Ile Leu Gln Thr Ile Ser
                325                 330                 335

Glu Gly Lys Phe Arg Thr Ala Asp Leu Gly Gly Lys Ala Ser Thr Ser
            340                 345                 350

Asp Phe Thr Lys Ala Val Cys Asp His Ile
            355                 360

<210> SEQ ID NO 5
<211> LENGTH: 1402
<212> TYPE: DNA
<213> ORGANISM: Glycine max

<400> SEQUENCE: 5
cggcacgagg tttgtaataa taataatttt agtttcttcg ttacgcctgc gttgtgcgtg      60
agaaagtgcg cgtggtgaaa accatggctt ctcagctcct gagacgaacc ttcggaagtc     120
gcatccttgc aaaccctagg gccttctcct tctcctccgc tgcttccact ccgatccgcg     180
ccactctctt ccccggcgac ggcatcggcc ccgagatcgc cgaatccgtc aaacagatat     240
tccaagcagc tgatgtccca atagaatggg aagagcacta tgtaggaact gaaattgacc     300
ctagaaccca agttttctg acatgggaaa gtttggaatc tgtaaggcaa aatgggttg      360 gcttgaaagg accaatggcc accctattg aaaagggca tcgttcatta aatcttactc      420
tgagaaaaga gctcaatttg tatgccaatg ttcgaccttg ctacagtctt ccaggctaca     480
aaactcggta tgataatgtc aatctaatca caattcgtga aaatacgaa ggcgagtaca      540 gtggacttga acatcaggtt gtgagaggtg tagtagaaag tctcaaaatc attacacgtc     600
aagcaagttt aagggtagct gagtatgctt ttcactatgc caaggctcat ggaagagaga     660
gggtttctgc catacacaaa gccaatatta tgcaaaagac tgatggcctt ttcctcaagt     720
gttgccgtga ggttgcagag aaatatcctg agataactta tgaggaagtt gtcattgaca     780
attgctgcat gatgcttgtg aagaatcctg cacttttcga tgtactagtg atgcctaacc     840
tttatggtga tattattagt gacctttgtg ctggcttggt tggggattgg ggtttaacac     900
caagctgcaa cattggcgag ggaggtattg cacttgctga ggctgtacat ggttcggcac     960
ctgatattgc tggaaagaat ttggcaaatc caactgcttt actgctaagt ggtgttacaa    1020
tgttgcgcca tttgaacctc catgacaaag cagaacagat tcaaaaagcc atcctgaaca    1080
caattgcaga agggaagtac cgaacagctg acctcggtgg cagttcaaag acaactgaat    1140
tcacaaaggc aattattgat catctttaga ttttggtttt ggagtcagca agaaattctt    1200
gcttatgatt ttgattttca gtcaattttc tatttattaa cccaattaat ccgaaagagt    1260
gggattacct cagcttaaag gaaaactcac ccatgtgtgt gacattttac aaccaaagac    1320
aaggaatggg caggctttca aatattcgct gcccttttca caatgcacatt gattgataaa    1380 aaaaaaaaaa aaaaaaaaaa aa                                             1402

<210> SEQ ID NO 6
<211> LENGTH: 361
<212> TYPE: PRT
<213> ORGANISM: Glycine max
```

```
<220> FEATURE:
<221> NAME/KEY: UNSURE
<222> LOCATION: (68)

<400> SEQUENCE: 6

Met Ala Ser Gln Leu Leu Arg Arg Thr Phe Gly Ser Arg Ile Leu Ala
 1               5                  10                  15

Asn Pro Arg Ala Phe Ser Phe Ser Ala Ala Ser Thr Pro Ile Arg
            20                  25                  30

Ala Thr Leu Phe Pro Gly Asp Gly Ile Gly Pro Glu Ile Ala Glu Ser
        35                  40                  45

Val Lys Gln Ile Phe Gln Ala Ala Asp Val Pro Ile Glu Trp Glu Glu
    50                  55                  60

His Tyr Val Xaa Thr Glu Ile Asp Pro Arg Thr Gln Ser Phe Leu Thr
65                  70                  75                  80

Trp Glu Ser Leu Glu Ser Val Arg Gln Asn Gly Val Gly Leu Lys Gly
                85                  90                  95

Pro Met Ala Thr Pro Ile Gly Lys Gly His Arg Ser Leu Asn Leu Thr
            100                 105                 110

Leu Arg Lys Glu Leu Asn Leu Tyr Ala Asn Val Arg Pro Cys Tyr Ser
        115                 120                 125

Leu Pro Gly Tyr Lys Thr Arg Tyr Asp Asn Val Asn Leu Ile Thr Ile
    130                 135                 140

Arg Glu Asn Thr Glu Gly Glu Tyr Ser Gly Leu Glu His Gln Val Val
145                 150                 155                 160

Arg Gly Val Val Glu Ser Leu Lys Ile Ile Thr Arg Gln Ala Ser Leu
                165                 170                 175

Arg Val Ala Glu Tyr Ala Phe His Tyr Ala Lys Ala His Gly Arg Glu
            180                 185                 190

Arg Val Ser Ala Ile His Lys Ala Asn Ile Met Gln Lys Thr Asp Gly
        195                 200                 205

Leu Phe Leu Lys Cys Cys Arg Glu Val Ala Glu Lys Tyr Pro Glu Ile
    210                 215                 220

Thr Tyr Glu Glu Val Val Ile Asp Asn Cys Cys Met Met Leu Val Lys
225                 230                 235                 240

Asn Pro Ala Leu Phe Asp Val Leu Val Met Pro Asn Leu Tyr Gly Asp
                245                 250                 255

Ile Ile Ser Asp Leu Cys Ala Gly Leu Val Gly Gly Leu Gly Leu Thr
            260                 265                 270

Pro Ser Cys Asn Ile Gly Glu Gly Gly Ile Ala Leu Ala Glu Ala Val
        275                 280                 285

His Gly Ser Ala Pro Asp Ile Ala Gly Lys Asn Leu Ala Asn Pro Thr
    290                 295                 300

Ala Leu Leu Leu Ser Gly Val Thr Met Leu Arg His Leu Asn Leu His
305                 310                 315                 320

Asp Lys Ala Glu Gln Ile Gln Lys Ala Ile Leu Asn Thr Ile Ala Glu
                325                 330                 335

Gly Lys Tyr Arg Thr Ala Asp Leu Gly Gly Ser Ser Lys Thr Thr Glu
            340                 345                 350

Phe Thr Lys Ala Ile Ile Asp His Leu
    355                 360
```

<210> SEQ ID NO 7
<211> LENGTH: 1492
<212> TYPE: DNA
<213> ORGANISM: Triticum sp.

<400> SEQUENCE: 7

| | | | | | |
|---|---|---|---|---|---|
| gcaagttggc | acccttttg | ctcccttcc | catccccatc | tttcgtccac | ccctcccccc | 60 |
| tctcgccgcg | gaccccatcc | gccgcccgcc | gccgccgccg | ttgacactac | ccgcgaatct | 120 |
| ccttcttccg | agtggtggag | aggagacatg | gcactccgga | ggctgcttca | ggggattgtc | 180 |
| ctaccgcgga | cgacgggccg | gcatgttggg | gcatcgtttt | ccacggaggc | tggggagact | 240 |
| atccgcgcaa | ccctgtttcc | cggtgatggc | atcgggcctg | agatcgccga | gtcggtcaag | 300 |
| caggtattca | atgttgcagg | tgtaccgata | gaatgggaag | aacattatgt | tggtacggaa | 360 |
| gttgatccca | gaacagagag | cttttgaca | tgggagagcc | tggagtctgt | gcgtagaaac | 420 |
| aaagttggct | tgaaaggtcc | tatggctaca | cctattggaa | aaggccaccg | ttctttgaat | 480 |
| cttacattaa | ggaaagaact | tggactctac | gccaatgtca | gaccttgcaa | cagcctccca | 540 |
| ggctacaaga | ctagatatga | tgatgtgaac | cttgtgacaa | tccgtgaaaa | tactgaagga | 600 |
| gagtatagtg | gccttgagca | tcaggttgtg | agggtgttg | tggaaagttt | gaaaattatt | 660 |
| acccgccaag | caagtttgag | agtggcagag | tatgcttcc | attatgccaa | agccaatggc | 720 |
| agggagaggg | tctctgcgat | acataaagct | aatatcatga | ggaaaacaga | cggactttc | 780 |
| ctcaagtgtt | gccgtgaagt | agctgagaag | taccctgaaa | tcacatatga | ggaagtcatt | 840 |
| attgacaatt | gctgcatgac | actcgtgaag | aatcctggta | catttgatgt | attagtgatg | 900 |
| ccaaatctgt | atggtgacat | tattagtgat | ctatgtgctg | gtttgatcgg | aggattgggc | 960 |
| ttaactccca | gctgcaacat | tggtgaaggt | ggcatttgtc | tggcagaggc | tgttcatggt | 1020 |
| tctgcacctg | atatctctgg | caagaaccttt | gcaaacccaa | ctgctcttat | gttgagtgct | 1080 |
| gttatgatgt | tgcgccactt | gcaattcaat | gaccaagcag | accggatcca | caatgccatc | 1140 |
| ctccagacaa | ttgccgaggg | gaagtacaga | accgctgatc | ttggtgggaa | gtcatcaaca | 1200 |
| tcagactaca | caaaagcagt | ttgcgatcat | atctgagcac | cagctgctct | ttctctcgat | 1260 |
| tatttgcctc | ccacctaatt | ttgttgcata | ccaggagctt | tagcctgagt | aggttaagtg | 1320 |
| gcaggcacct | cgatttcctt | gggtgttaag | acaccattta | aggctcctga | ataaatctcg | 1380 |
| cattcttgtc | cttggaaaag | ttttaccagc | attgcagtca | agctgaagaa | tcgtatgtaa | 1440 |
| taatcattgg | cagcatcagc | gcatataatt | tgttaaaaaa | aaaaaaaaaa | aa | 1492 |

<210> SEQ ID NO 8
<211> LENGTH: 362
<212> TYPE: PRT
<213> ORGANISM: Triticum sp.

<400> SEQUENCE: 8

Met Ala Leu Arg Arg Leu Leu Gln Gly Ile Val Leu Pro Arg Thr Thr
1               5                   10                  15

Gly Arg His Val Gly Ala Ser Phe Ser Thr Glu Ala Gly Glu Thr Ile
            20                  25                  30

Arg Ala Thr Leu Phe Pro Gly Asp Gly Ile Gly Pro Glu Ile Ala Glu
        35                  40                  45

Ser Val Lys Gln Val Phe Asn Val Ala Gly Val Pro Ile Glu Trp Glu
    50                  55                  60

Glu His Tyr Val Gly Thr Glu Val Asp Pro Arg Thr Glu Ser Phe Leu
65                  70                  75                  80

-continued

```
Thr Trp Glu Ser Leu Glu Ser Val Arg Arg Asn Lys Val Gly Leu Lys
                85                  90                  95

Gly Pro Met Ala Thr Pro Ile Gly Lys Gly His Arg Ser Leu Asn Leu
            100                 105                 110

Thr Leu Arg Lys Glu Leu Gly Leu Tyr Ala Asn Val Arg Pro Cys Asn
        115                 120                 125

Ser Leu Pro Gly Tyr Lys Thr Arg Tyr Asp Asp Val Asn Leu Val Thr
    130                 135                 140

Ile Arg Glu Asn Thr Glu Gly Glu Tyr Ser Gly Leu Glu His Gln Val
145                 150                 155                 160

Val Arg Gly Val Val Glu Ser Leu Lys Ile Ile Thr Arg Gln Ala Ser
                165                 170                 175

Leu Arg Val Ala Glu Tyr Ala Phe His Tyr Ala Lys Ala Asn Gly Arg
            180                 185                 190

Glu Arg Val Ser Ala Ile His Lys Ala Asn Ile Met Arg Lys Thr Asp
        195                 200                 205

Gly Leu Phe Leu Lys Cys Cys Arg Glu Val Ala Glu Lys Tyr Pro Glu
    210                 215                 220

Ile Thr Tyr Glu Glu Val Ile Ile Asp Asn Cys Cys Met Thr Leu Val
225                 230                 235                 240

Lys Asn Pro Gly Thr Phe Asp Val Leu Val Met Pro Asn Leu Tyr Gly
                245                 250                 255

Asp Ile Ile Ser Asp Leu Cys Ala Gly Leu Ile Gly Gly Leu Gly Leu
            260                 265                 270

Thr Pro Ser Cys Asn Ile Gly Glu Gly Gly Ile Cys Leu Ala Glu Ala
        275                 280                 285

Val His Gly Ser Ala Pro Asp Ile Ser Gly Lys Asn Leu Ala Asn Pro
    290                 295                 300

Thr Ala Leu Met Leu Ser Ala Val Met Met Leu Arg His Leu Gln Phe
305                 310                 315                 320

Asn Asp Gln Ala Asp Arg Ile His Asn Ala Ile Leu Gln Thr Ile Ala
                325                 330                 335

Glu Gly Lys Tyr Arg Thr Ala Asp Leu Gly Gly Lys Ser Ser Thr Ser
            340                 345                 350

Asp Tyr Thr Lys Ala Val Cys Asp His Ile
        355                 360

<210> SEQ ID NO 9
<211> LENGTH: 364
<212> TYPE: PRT
<213> ORGANISM: Nicotiana tabacum

<400> SEQUENCE: 9

Met Ala Phe Gln Ile Ala Arg Arg Leu Leu Arg Ser Arg Ala Ser Ser
  1               5                  10                  15

Ser Ile Arg Tyr Leu Asp Arg Ser Phe Ser Ser Glu Ser Asn Ser Asn
                20                  25                  30

Leu Ile Arg Ala Thr Leu Phe Pro Gly Asp Gly Ile Gly Pro Glu Ile
            35                  40                  45

Ala Asp Ser Val Arg Gln Ile Phe Lys Thr Ala Glu Val Pro Ile Glu
        50                  55                  60

Trp Glu Glu His Tyr Val Gly Lys Glu Ile Asp Pro Arg Thr Asn Ser
65                  70                  75                  80

Phe Leu Thr Trp Glu Ser Leu Glu Ser Val Arg Arg Asn Lys Val Gly
                85                  90                  95
```

```
Leu Lys Gly Pro Met Ala Thr Pro Ile Gly Lys Gly His Arg Ser Leu
            100                 105                 110

Asn Leu Thr Leu Arg Lys Glu Leu Asn Leu Tyr Ala Asn Val Arg Pro
        115                 120                 125

Cys Tyr Ser Leu Pro Gly Tyr Lys Thr Arg Tyr Asp Asp Val Asn Leu
    130                 135                 140

Ile Thr Ile Arg Glu Asn Thr Glu Gly Glu Tyr Ser Gly Val Glu His
145                 150                 155                 160

Gln Val Val Arg Gly Val Val Glu Ser Leu Lys Ile Ile Thr Arg Gln
                165                 170                 175

Ala Ser Leu Arg Val Ala Glu Tyr Ala Phe His Tyr Ala Lys Ala His
            180                 185                 190

Gly Arg Glu Arg Val Ser Ala Ile His Lys Ala Asn Ile Met Gln Lys
        195                 200                 205

Thr Asp Gly Leu Phe Leu Lys Cys Cys Arg Glu Val Ala Glu Lys Tyr
    210                 215                 220

Pro Glu Ile Lys Tyr Glu Val Val Ile Asp Asn Cys Cys Met Met
225                 230                 235                 240

Leu Val Lys Asn Pro Ala Leu Phe Asp Ile Leu Val Met Pro Asn Leu
                245                 250                 255

Tyr Gly Asp Ile Ile Ser Asp Leu Cys Ala Gly Val Ile Gly Gly Leu
            260                 265                 270

Gly Leu Thr Pro Ser Cys Asn Ile Gly Glu Gly Ile Ala Leu Ala
        275                 280                 285

Glu Ala Val His Gly Ser Ala Pro Asp Ile Ala Gly Lys Asn Leu Ala
    290                 295                 300

Asn Pro Thr Ala Leu Leu Leu Ser Ala Val Thr Met Leu Arg His Leu
305                 310                 315                 320

Glu Leu His Asp Lys Ala Asp Arg Ile Gln Gly Ala Val Leu Asn Thr
                325                 330                 335

Ile Ala Glu Gly Lys Tyr Arg Thr Gly Asp Leu Gly Gly Thr Ser Ser
            340                 345                 350

Thr Thr Asp Phe Thr Asn Ala Ile Cys Asp His Leu
        355                 360

<210> SEQ ID NO 10
<211> LENGTH: 357
<212> TYPE: PRT
<213> ORGANISM: Solanum tuberosum

<400> SEQUENCE: 10

Met Ala Leu Gln Ile Ala Lys Arg Leu Leu Arg Cys Arg Ala Asp Ser
1               5                   10                  15

Val Ala Ser Ser Val Arg Phe Phe Asp Arg Thr Phe Thr Ser Glu Ser
                20                  25                  30

Asn Ser Asn Leu Ile Arg Ala Thr Leu Phe Pro Gly Asp Gly Ile Gly
            35                  40                  45

Pro Glu Ile Ala Glu Ser Val Arg Gln Ile Phe Lys Val Ala Glu Val
        50                  55                  60

Pro Ile Glu Trp Glu Glu His Tyr Val Gly Thr Glu Val Asp Pro Arg
65                  70                  75                  80

Thr Asn Ser Phe Leu Thr Trp Glu Ser Leu Glu Ser Val Arg Arg Asn
                85                  90                  95

Lys Val Gly Leu Lys Gly Pro Met Ala Thr Pro Ile Gly Lys Gly His
            100                 105                 110
```

-continued

```
Arg Ser Leu Asn Leu Thr Leu Arg Lys Glu Leu Asn Leu Tyr Ala Asn
        115                 120                 125

Val Arg Pro Cys Tyr Ser Leu Pro Gly Tyr Lys Thr Arg Tyr Asp Asp
    130                 135                 140

Val Asn Leu Ile Thr Ile Arg Glu Asn Thr Glu Gly Glu Tyr Ser Gly
145                 150                 155                 160

Leu Glu His Gln Val Val Arg Gly Val Val Glu Ser Leu Lys Ile Ile
                165                 170                 175

Thr Arg Gln Ala Ser Leu Arg Val Ala Glu Tyr Ala Phe His Tyr Ala
            180                 185                 190

Lys Thr His Gly Arg Glu Arg Val Ser Ala Ile His Lys Ala Asn Ile
        195                 200                 205

Met Gln Lys Thr Asp Gly Leu Phe Leu Lys Cys Cys Arg Glu Val Ala
    210                 215                 220

Glu Lys Tyr Pro Glu Ile Lys Tyr Glu Glu Val Val Ile Asp Asn Cys
225                 230                 235                 240

Cys Met Met Leu Val Lys Asn Pro Ala Leu Phe Asp Val Leu Val Met
                245                 250                 255

Pro Asn Leu Tyr Gly Asp Ile Ile Ser Asp Leu Cys Ala Gly Leu Ile
            260                 265                 270

Gly Gly Leu Gly Leu Thr Pro Ser Cys Asn Ile Gly Glu Gly Gly Ile
        275                 280                 285

Ala Leu Ala Glu Ala Val His Gly Ser Ala Pro Asp Ile Ala Gly Lys
    290                 295                 300

Asn Leu Ala Asn Pro Thr Ala Leu Leu Leu Ser Ser Val Ser Met Leu
305                 310                 315                 320

Arg His Leu Glu Leu His Asp Lys Ala Asp Arg Ile Gln Asp Ala Ile
                325                 330                 335

Leu Lys Thr Ile Ala Gly Gly Lys Val Pro Asn Trp Arg Pro Trp Arg
            340                 345                 350

His Cys Tyr Asn Asn
        355
```